US007053253B1

(12) United States Patent
Zhang et al.

(10) Patent No.: US 7,053,253 B1
(45) Date of Patent: May 30, 2006

(54) PROCESS FOR PURIFYING HEXAFLUOROPROPENE DIMERS

(75) Inventors: Zhongxing Zhang, Woodbury, MN (US); Zai-Ming Qiu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/120,024

(22) Filed: May 2, 2005

(51) Int. Cl.
C07C 17/395 (2006.01)
C07C 17/38 (2006.01)
C07C 17/383 (2006.01)

(52) U.S. Cl. .................. 570/177; 570/171; 570/172; 570/175; 570/178

(58) Field of Classification Search ................ 570/177, 570/171, 172, 175, 178
See application file for complete search history.

(56) References Cited

U.S. PATENT DOCUMENTS

| | | | |
|---|---|---|---|
| 2,918,501 A | 12/1959 | Brehm et al. | |
| 3,185,734 A | 5/1965 | Fawcett et al. | |
| 3,917,724 A | 11/1975 | Martini | |
| 4,296,265 A | 10/1981 | Ohsaka et al. | |
| 4,377,717 A | 3/1983 | Anello et al. | |
| 4,535,184 A | 8/1985 | Middleton | |
| 5,254,774 A | 10/1993 | Prokop | |
| 5,387,728 A | 2/1995 | Gisser et al. | |
| 5,557,020 A * | 9/1996 | Von Werner | ................ 570/177 |
| 6,774,270 B1 | 8/2004 | Zhang et al. | |

FOREIGN PATENT DOCUMENTS

JP 62-46528 10/1987

OTHER PUBLICATIONS

Rodriguez, "*Principles of Polymer Systems, Basic Structures of Polymers*", (1982), pp. 23-27, 2nd Edition, Hemisphere Publishing Corporation, New York.

Rodriguez, "*Principles of Polymer Systems*", (1986), pp. 28-32, 3rd Edition, Hemisphere Publishing Corporation, New York.

Huang et al., "*Oligomerization of Perfluoropropylene Catalyzed by π-Bis(Arene)Chromium(0) Complexes*", Journal of Organometallic Chemistry, (1981), pp. 164-175, vol. 218, Elsevier Sequoia S.A., Lausanne.

Von Halasz et al., "*Darstellung und Fluorierung von Oligomeren des Hexafluorpropens*", Chem. Ber., (1973), pp. 2950-2959, vol. 106, No. 9.

Smith et al., "*The Chemistry of Carbonyl Fluoride. II. Synthesis of Perfluoroisopropyl Ketones*", Perfluoroisopropyl Ketones, (Nov. 20, 1962), pp. 4285-4288, vol. 84.

Dresdner et al., "*Alkali Fluorides as Catalysts in Reactions Involving Unsaturated Fluorocarbons*", Alkali Fluoride Catalyzed Fluorocarbon Reactions, (Oct. 1965), pp. 3524-3527, vol. 30.

Probst et al., "*Synthesis and Chemistry of Perfluoro-2-Iodo-2 Methyl-Alkanes*", Journal of Fluorine Chemistry, (1987), pp. 223-245, vol. 37, Elsevier Sequoia.

Barton, "*CRC Handbook of Solubility Parameters and Other Cohesion Parameters*", (1991), 2nd Edition, CRC Press Inc., Boca Raton, FL.

Martini et al., "*About the Reaction of Hexafluoropropylene and Perfluoro-2-Methyl-2-Pentene with Water*", Journal of Fluorine Chemistry, (1976), pp. 535-540, vol. 8.

* cited by examiner

*Primary Examiner*—Elvis O. Price
(74) *Attorney, Agent, or Firm*—Kent S. Kokko

(57) ABSTRACT

Perfluoro-4-methyl-2-pentene containing the undesirable perfluoro-2-methyl-2-pentene may be purified by contacting the mixture with at least a stoichiometric equivalent of an aqueous inorganic base (relative to the perfluoro-2-methyl-2-pentene), in the presence of a polar solvent.

23 Claims, No Drawings

PROCESS FOR PURIFYING HEXAFLUOROPROPENE DIMERS

FIELD OF THE INVENTION

The present invention is related to the purification of hexafluoropropene dimers, and removal of toxic isomers therefrom.

BACKGROUND

Hexafluoropropene dimers and higher oligomers are useful as solvents and as reactive intermediates for the preparation of monomers, surfactants, and other materials such as textile treating agents, paper treating agents, and potting compounds. More recently, fluorinated fluids derived from hexafluoropropylene have been proposed as replacements for chlorofluorocarbons (CFCs) in applications such as coolants for electronic devices (e.g., supercomputers), inert solvents and fluids, fire-extinguishing agents, blowing agent in the production of foams and as heat transfer agents.

As noted in U.S. Pat. No. 5,387,728 (Gisser et al.), hexafluoropropene dimer is a pure fluorocarbon compound and is chlorine-free and thus does not influence the ozone layer in the stratosphere, in contrast to CFC 113. The ozone degradation potential (ODP) is equal to zero. Because of its relatively reactive double bond, its life in the atmosphere is shorter than that of the saturated perfluoroalkanes that are likewise useful as CFC 113 substitutes. Because of its low acute mammalian (oral) toxicity, bacterial toxicity and fish toxicity, but poor biological degradability, the hexafluoropropene dimer is only a slight hazard to water. As noted in Probst et al., J. Fluorine Chem, 37 (1987) 223–245, some HFP dimers may represent an exposure hazard due to their toxicity.

Hexafluoropropene dimers and higher oligomers have been prepared by both gas-phase and liquid-phase processes involving a variety of catalysts. The dimerization typically yields varying ratios of the kinetic isomers; cis- and trans-perfluoro-4-methyl-2-pentene, and minor amounts of the toxic thermodynamic isomer; perfluoro-2-methyl-2-pentene, as well as higher oligomers.

SUMMARY OF THE INVENTION

The present invention provides a process for purifying perfluoro-4-methyl-2-pentene containing the undesirable perfluoro-2-methyl-2-pentene (both dimers of hexafluoropropene) comprising contacting the mixture with at least a stoichiometric equivalent of an aqueous inorganic base relative to the perfluoro-2-methyl-2-pentene, and a polar solvent.

"HFP dimer" refers to unsaturated compounds of the formula $C_6F_{12}$, formed by the dimerization of hexafluoropropylene. HFP dimers are suitable in many areas of use as a replacement for chlorofluorocarbons, which are held responsible for the degradation of the ozone in the stratosphere. Considerable amounts of perfluoro-2-methyl-2-pentene, on account of its toxicity, would obviously be unwanted in a substitute product. It is therefore desirable to prepare dimers of hexafluoropropene having as high as possible a proportion of perfluoro-4-methyl-2-pentene and as low as possible a proportion of perfluoro-2-methyl-2-pentene.

The instant process is selective toward removal of the undesirable species, and largely unreactive toward the desired species. The process uses mild conditions and readily available reagents, and can reduce the amount of the undesirable perfluoro-2-methyl-2-pentene to levels below 1000 ppm, preferably below 100 ppm and most preferably below 10 ppm, so that the resultant purified product is suitable for the intended end-use applications. The purified perfluoro-4-methyl-2-pentene is then readily separated from the reaction products of the undesirable perfluoro-2-methyl-2-pentene.

DETAILED DESCRIPTION

Hexafluoropropylene (HFP), in the presence of a suitable catalyst such as fluoride anion, forms a heptafluoropropylene anion of the formula $(CF_3)_2CF^-$ that may add to suitable electrophiles, such as hexafluoropropylene itself, to form dimers, trimers and higher molecular weight oligomers.

In general, the kinetic dimer isomers of HFP form quickly in the presence of fluoride ion, and are converted to the thermodynamic dimer over time. The HFP dimers have two kinetic isomers and a thermodynamic isomer of the following structures:

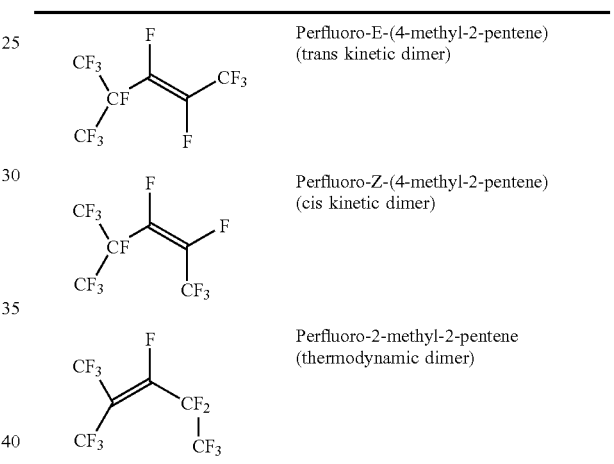

The starting mixture of hexafluoropropene dimers may be prepared by any available method. Hexafluoropropene dimers have been prepared by both gas-phase and liquid-phase processes involving a variety of catalysts. The dimerization may yield varying ratios of the kinetic isomers; cis- and trans-perfluoro-4-methyl-2-pentene, and minor amounts of the toxic thermodynamic isomer; perfluoro-2-methyl-2-pentene, as well as higher oligomers. Under uncontrolled conditions, the undesirable isomer may predominate.

Gas-phase hexafluoropropene oligomerization processes are solventless processes which have utilized catalysts such as alkali metal fluorides (see, for example, Dresdner et al., J. Org. Chem. 30, 3524 (1965)), activated carbon (see, for example, U.S. Pat. No. 4,377,717 (Anello et al.)), and alkali metal fluoride supported on activated charcoal or nickel oxide (see, for example, U.S. Pat. No. 4,296,265 (Ohsaka et al.)). These processes involve contacting gaseous hexafluoropropene with the catalyst at elevated temperature.

Liquid-phase hexafluoropropene oligomerization processes have utilized aprotic solvents and catalysts such as metal halides (preferably fluorides and bifluorides) and hydroxides (see, for example, U.S. Pat. No. 2,918,501 (Brehm et al.)), ammonium fluoride (see, for example, Japanese Patent Publication No. 87-046528 (Neos KK)), fluorine-containing amines (see, for example, U.S. Pat. No.

3,917,724 (Martini) and von Halasz et al., Chem. Ber. 106(9), 2950 (1973)), quaternary ammonium salts (see, for example, Brehm et al., supra), π-bis(arene)chromium(0) complexes (see, for example, Huang et al., J. Organometal. Chem. 218, 164 (1981)), and tris(disubstituted amino)sulfonium perfluorocarbanion salts (see, for example, U.S. Pat. No. 4,535,184 (Middleton)). These processes involve contacting hexafluoropropene with the catalyst-solvent combination.

A process for preparing dimers of hexafluoropropene with a high proportion of trans-perfluoro-4-methyl-2-pentene and minor amounts of perfluoro-2-methyl-2-pentene has been described in U.S. Pat. No. 5,387,728 (Gisser et al.), wherein the dimerization of the hexafluoropropene is carried out in an aprotic solvent in the presence of an adduct of an amine which contains no NH groups and a metal fluoride. This process purportedly yields HFP dimer products in which the content of perfluoro-2-methyl-2-pentene has been reduced to as little as 0.2%.

A preferred method of preparing the HFP dimers comprises contacting hexafluoropropene with a catalyst or a mixture of catalysts selected from the group consisting of the cyanide, cyanate, and thiocyanate salts of alkali metals, quaternary ammonium, and quaternary phosphonium, in the presence of polar, aprotic solvent, e.g., acetonitrile. The process of the invention is especially useful for selectively preparing hexafluoropropene dimers, e.g., perfluoro-2-methyl-2-pentene and perfluoro-4-methyl-2-pentene, in good yield by the proper choice of solvent and catalyst. Reference may be made to U.S. Pat. No. 5,254,774 (Prokop), incorporated herein by reference.

Alternatively, HFP dimers are commercially available. For example, perfluoro-4-methyl-2-pentene containing 5~10% perfluoro-2-methyl-2-pentene is available from Lancaster Synthesis Inc. (Windham, N.H.) or SynQuest Laboratories, Inc. (Alachua, Fla.).

In the process of the invention, a mixture of HFP dimers is contacted with an aqueous inorganic base in the presence of a polar organic solvent. The amount of inorganic base is present in at least a stoichiometric amount relative to the amount of the undesirable perfluoro-2-methyl-2-pentene present in the mixture. Generally, the amount of base is 1 to 300 times the molar equivalent of the undesirable perfluoro-2-methyl-2-pentene. Preferably, the amount of base is 100 to 200 times the molar equivalent of the perfluoro-2-methyl-2-pentene. The aqueous base may be used in any concentration, but is generally at least 10% by weight in water. Higher concentrations of aqueous base (e.g. at least 20%, at least 30% or at least 40%) are preferred.

Useful inorganic bases include, but are not limited to, metal, alkali metal and alkali earth metal hydroxides, carbonates, bicarbonates, or an alkali- or alkali-earth metal phosphates. Particularly useful inorganic bases are alkali and alkali earth metal hydroxides including potassium hydroxide, and sodium hydroxide, cesium hydroxide, lithium hydroxide, calcium hydroxide, magnesium hydroxide, and barium hydroxide. Applicants have found that organic bases tend to promote isomerization of the kinetic isomers to the undesirable thermodynamic isomer and are therefore less effective in the instant process.

The mixture of HFP dimers is contacted with an aqueous inorganic base in the presence of a polar organic solvent. Any volume of solvent may be used relative to the volume of the HFP mixture, but amounts in excess of the solubility limit of the polar organic solvent in the HFP dimer mixture confers no additional benefits; the excess separates from the mixture as a separate phase. Generally, the polar organic solvent is used in amounts of from 0.1 to 10 volume percent relative to said HFP dimer mixture. Solvents are chosen to be essentially nonreactive with the dimers under the process conditions. A mixture of solvents may be used.

An important property of polar solvents to be considered is the Hildebrand solubility parameter, "$\delta$". The constant gives a rough guide to solvent properties. "Hildebrand solubility parameter" refers to a solubility parameter represented by the square root of the cohesive energy density of a material, having units of pressure$^{1/2}$, and being equal to $((\Delta H - RT)/V)^{1/2}$ where $\Delta H$ is the molar vaporization enthalpy of the material, R is the universal gas constant, T is the absolute temperature, and V is the molar volume of the solvent. Hildebrand solubility parameters are tabulated for solvents in F. Rodriguez, Ed., Principles of Polymer Systems, $3^{rd}$ Edition, Hemisphere Publishing Corp., 1986, pp. 28–32. Reference may also be made to Barton, A. F. M., Handbook of Solubility and Other Cohesion Parameters, $2^{nd}$ Ed., CRC Press, Boca Raton, Fla. (1991). Useful solvents have a Hildebrand solubility parameter of at least 7.4 $(cal/cm^3)^{1/2}$ (~15.1 $(J/cm^3)^{1/2}$) and preferably at least 9.1 $(cal/cm^3)^{1/2}$ (~18.6 $(J/cm^3)^{1/2}$).

Useful solvents will also be at least partially soluble in water in the amounts used (i.e. the amount of water added with the aqueous inorganic base), and preferably the organic solvent will have a solubility of at least 6 grams/100 grams water. More preferably the organic solvent will be soluble in all proportions in water.

Suitable solvents include, for example, alcohols such as 2-propanol, sec-butanol and t-butanol, ketones such as acetone and methyl ethyl ketone, aldehydes such as formaldehyde, acetaldehyde, propionaldehyde, acrolein, glutaraldehyde and 2-hydroxy-adipaldehyde, amides such as acetamide and N,N-dimethylformamide, ethers such as diethyl ether, ethylene glycol dimethyl ether, dioxane, tetrahydrofuran and diethylene glycol dimethyl ether; carboxylic acid esters such as methyl formate, ethyl formate, ethyl acetate, methyl acetate, diethyl carbonate, propylene carbonate, and ethylene carbonate; alkyl nitriles such as acetonitrile; alkyl amides such as N,N-dimethylformamide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and mixtures thereof. Under some reaction conditions some primary alcohols may be reactive with the HFP dimers, and therefore secondary and tertiary alcohols are preferred.

Most preferably solvents include those polar solvents having a Hildebrand Solubility Parameter of 9.1 $(cal/cm^3)^{1/2}$ and above. Suitable polar solvents include acetone, acetonitrile, tbutyl alcohol, carbon disulfide, N,N'-diformylpiperazine, N,N-dimethylacetamide, N,N-dimethylformamide, dimethyl sulfoxide, 1,4-dioxane, ethyl acetate, ethylene carbonate, formamide, furfural, isopropyl alcohol, methyl ethyl ketone, and tetrahydrofuran.

In the process of the invention, the HFP dimer mixture is contacted with the aqueous base and the polar organic solvent at a temperature and for a time sufficient to reduce the amount of perfluoro-2-methyl-2-pentene below a predetermine level. Generally, the perfluoro-2-methyl-2-pentene is reduced to below 1000 ppm, preferably below 100 ppm, and most preferably below 10 ppm.

The process may be conducted at any desirable temperature, but is preferably below 100° C., more preferably below 50° C. and most preferably at ambient temperature (15 to 30° C.). Heating of the reaction mixture may reduce the selectivity for removal of the undesirable perfluoro-2-methyl-2-pentene, so that the yield of the desirable perfluoro-4-methyl-2-pentene isomer is reduced. Lower temperatures may result in rates too slow for a commercial process.

The time required is dependent on the inorganic base concentration, the amount of undesirable dimer present, the volume of fluid to be treated and the temperature, which are generally selected so the undesirable isomer is reduced to a desired level in less than a day, preferably in 1 to 6 hours time, with sufficient stirring or agitation of the mixture.

The process may be monitored by conventional analytic means, such as gas chromatography, mass spectroscopy, $^{13}C$ and $^{19}F$ NMR.

It is believed that the undesirable isomer (I) reacts with the inorganic base present to form an enolate (II) of a perfluorinated ketone (perfluoro(ethyl isopropyl ketone, III)). The ketone (III) is further in equilibrium with the ketal (IV). It is believed that the equilibrium greatly favors the enolate (II), although all the isomers are readily separated from the desired product. The cation corresponding to the inorganic base is not shown.

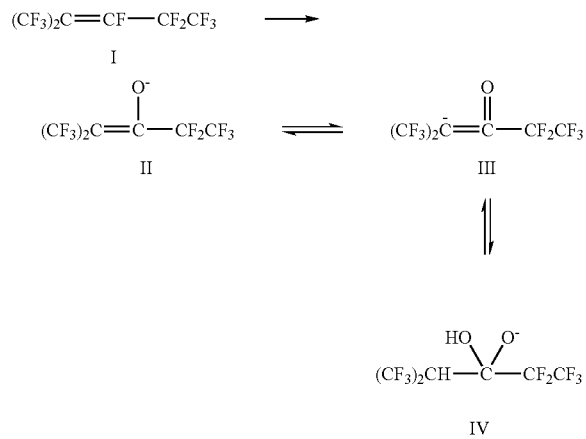

Advantageously, the perfluorinated enolate (tautomers II and III) and the ketal (IV) derived from the undesirable perfluoro-2-methyl-2-pentene are water soluble, while the desirable perfluoro-4-methyl-2-pentene is not. The perfluorinated enolate may be separated from solution using conventional means known to the art.

In one embodiment, the fluid to be treated comprises a solvent in which the perfluoro-4-methyl-2-pentene or the perfluorinated enolate is soluble, but not both. In this embodiment, for example, a solvent is chosen so that the perfluorinated enolate is soluble in the chosen solvent (such as water), but the desired perfluoro-4-methyl-2-pentene is not. Alternatively, the solvent may be chosen so that the desired perfluoro-4-methyl-2-pentene is soluble in the chosen solvent, but the perfluorinated enolate is not. In another embodiment, the fluid to be treated is contacted with silica or alumina having a preferential affinity for the perfluorinated enolate.

In a preferred embodiment, the perfluorinated enolate may precipitate or "phase-split" from the treated fluid and may be separated by decantation. Generally, water may be added to the treated mixture so that the desired perfluoro-4-methyl-2-pentene separates as a separate phase, and the perfluorinated enolate dissolves in the aqueous phase. If desired, the aqueous phase may be subsequently treated with acid to convert the perfluorinated enolate to the perfluorinated ketone, which may then be isolated and recovered.

In another preferred embodiment, the treated mixture may be distilled so that the low boiling perfluoro-4-methyl-2-pentene (b.p. 46~49° C., from U.S. Pat. No. 5,557,020), as the perfluorinated enolate is not readily distilled from the reaction mixture. Advantageously, a simple one-plate distillation apparatus is sufficient to effect separation; multiplate distillation columns are not required.

The perfluoro-4-methyl-2-pentene obtainable according to the invention (as a mixture of cis- and trans-isomers) is particularly suitable for use as a heat transfer, cooling and insulation medium, especially for two-phase evaporative cooling of electrical and electronic components, for example as cooling medium for the two-phase evaporative cooling of gases or liquids without high-voltage insulation, preferably in a heat exchanger tube, or as a heat transfer medium where the heat energy passes by single-phase convection from the gaseous, liquid or solid material to be cooled to another gaseous, liquid or solid material to be heated. The purified perfluoro-4-methyl-2-pentene is also useful in foam blowing applications, both as a blowing agent per se, and as a nucleating additive used in combination with conventional blowing agents.

Further, the purified dimer is suitable as a reagent in the preparation of other fluorinated materials. As known, hexafluoropropylene dimer will form the weakly nucleophilic anion, which may add to a strongly electrophilic compound to form useful fluorinated products. Useful electrophiles include other fluorinated olefins such as tetrafluoroethylene, perfluorobutene, perfluorinated-, nonfluorinated- or partially fluorinated acyl compounds, including, acyl halides, esters, and anhydrides; and fluorinated aromatic compounds. Fluorinated ketones (i.e., perfluoroketones) may be prepared as described in, for example, U.S. Pat. No. 3,185,734 (Fawcett et al.) and J. Am. Chem. Soc., v. 84, pp. 4285–88, 1962, by addition to a perfluoroacyl halide (e.g., $CF_3CF_2COF$) in an anhydrous environment (e.g., in diethylene glycol dimethyl ether, or "diglyme") in the presence of anhydrous fluoride ion at an elevated temperature, typically at around 50 to 80° C.

Objects and advantages of this invention are further illustrated by the following examples, but the particular materials and amounts thereof recited in these examples, as well as other conditions and details, should not be construed to unduly limit this invention.

EXAMPLES

For the purposes of the following examples, all solvents and reagents were obtained from Sigma Aldrich, Milwaukee, Wis. All percentages are reported as an area % of a gas chromatography flame ionization detector analysis (GC-FID). This area % very closely approximated the weight percent. For very low concentrations, the weight percent was reported as parts per million (ppm).

Hexafluoropropene dimer (HFPD) used in the following examples was prepared according to U.S. Pat. No. 5,254,774. Analysis of this material showed 92.32% trans-perfluoro-(4-methyl-2-pentene) (designated HFPD I-trans), 4.66% cis-perfluoro-(4-methyl-2-pentene) (designated HFPD I-cis) and 622 ppm perfluoro-(2-methyl-2-pentene) (designated HFPD II). Other major components included hexafluoropropene trimers (total 2.4990% from 5 isomers), hexafluoropropene (1958 ppm) and $C_3F_7H$ (2296 ppm).

Examples 1–14 and Comparative Examples C1–C4

A 25 ml bottle was charged with 10 g HFPD as prepared above. Aqueous base and solvent were added to the bottle in amounts noted in Table 1 below. The bottle was sealed and the contents were reacted at room temperature for two hours with magnetic stirring. Following the reaction, 10 g of water was added and the mixture was shaken for 10 seconds. The lower organic phase was then isolated and analyzed by GC-FID. The results are summarized in Table 1 below.

TABLE 1

Examples 1–14 and Comparative Examples C1–C4

| Example | Base | Solvent | HFPD I-trans | HFPD I-cis | HFPD (II) |
|---|---|---|---|---|---|
| 1 | 0.5 g KOH (45%) | 0.2 g $CH_3CN$ | 92.87% | 4.66% | 0 ppm |
| 2 | 0.5 g KOH (45%) | 0.15 g $CH_3CN$ | 92.67% | 4.65% | 0 ppm |
| 3 | 0.5 g KOH (45%) | 0.1 g $CH_3CN$ | 93.32% | 4.69% | 0 ppm |
| 4 | 0.5 g KOH (45%) | 0.079 g $CH_3CN$ | 93.41% | 4.68% | 0 ppm |
| 5 | 0.5 g KOH (45%) | 0.039 g $CH_3CN$ | 92.67% | 4.63% | 0 ppm |
| 6 | 0.5 g KOH (45%) | 0.00786 g $CH_3CN$ | 92.43% | 4.68% | 312 ppm |
| 7 | 0.5 g KOH (45%) | 0.1 g $CH_3O(CH_2)_2OCH_3$ | 93.52% | 4.65% | 0 ppm |
| 8 | 0.5 g NaOH (42%) | 0.14 g $CH_3CN$ | 93.06% | 4.70% | 0 ppm |
| 9 | 0.5 g LiOH (~10%) | 0.14 g $CH_3CN$ | 92.55% | 4.64% | 0 ppm |
| 10 | 0.5 g KOH (45%) | 0.1 g $(CH_3)_2CHOH$ | 93.81% | 4.72% | 0 ppm |
| 11 | 0.5 g KOH (45%) | 0.1 g $CH_3CN$/0.1 g 1,4-dioxane | 92.55% | 4.64% | 0 ppm |
| 12 | 0.5 g KOH (45%) | 0.1 g $CH_3CN$/0.1 g $(CH_3)_2CHOH$ | 93.09% | 4.69% | 0 ppm |
| 13 | 0.5 g KOH (45%) | 0.1 g $CH_3CN$/0.1 g $CH_3O(CH_2)_2OCH_3$ | 92.86% | 4.65% | 0 ppm |
| 14 | 0.5 g KOH (45%) | 0.1 g $CH_3CN$/0.1 g $HCON(CH_3)_2$ | 92.04% | 4.61% | 0 ppm |
| C-1 | 0.5 g KOH (45%) | None | 92.42% | 4.63% | 717 ppm |
| C-2 | 0.5 g $(iPr)_2NEt$* | None | 92.42% | 4.68% | 604 ppm |
| C-3 | 0.5 g $(i-Pr)_2NEt$ | 0.25 g $H_2O$ | 92.39% | 4.67% | 589 ppm |
| C-4 | 0.5 g DBU** | None | 92.81% | 4.61% | 1321 ppm |

*$(iPr)_2NEt = ((CH_3)_2CH)_2NCH_2CH_3$
**DBU = 1 8-diazobicyclo[5.4.0]undec-7-ene

What is claimed is:

1. A process for purifying perfluoro-4-methyl-2-pentene containing perfluoro-2-methyl-2-pentene comprising contacting the mixture comprising:
   a) at least a stoichiometric equivalent of an aqueous inorganic base relative to the perfluoro-2-methyl-2-pentene, and
   b) a polar solvent.

2. The process of claim 1 comprising a stoichiometric excess of inorganic base relative to the amount of perfluoro-2-methyl-2-pentene.

3. The process of claim 2 wherein said inorganic base is from 1 to 300 times the molar equivalent of said perfluoro-2-methyl-2-pentene.

4. The process of claim 2 wherein said inorganic base is selected from metal, alkali metal and alkali earth metal hydroxides, carbonates, bicarbonates, or an alkali- or alkali-earth metal phosphates.

5. The process of claim 2 wherein said aqueous inorganic base is at least 10 wt. % in water.

6. The process of claim 1 wherein said polar solvent has a Hildebrand solubility parameter of at least 7.4 $(cal/cm^3)^{1/2}$ (~15.1 $(J/cm^3)^{1/2}$).

7. The process of claim 1 wherein said polar solvent has a Hildebrand solubility parameter of at least 9.1 $(cal/cm^3)^{1/2}$ (~18.6 $(J/cm^3)^{1/2}$).

8. The process of claim 1 wherein said polar solvent is used in an amount from 0.1 to 10 volume percent relative to said hexafluoropropene dimer mixture.

9. The process of claim 1 wherein said polar solvent is selected from carboxylic acid esters; ethers, ketones, alkyl nitrites; alkyl amides; alkyl sulfoxides; alkyl sulfones; oxazolidones, secondary and tertiary alcohols, and mixtures thereof.

10. The process of claim 1 wherein the amount of perfluoro-2-methyl-2-pentene is reduced to less than 1000 ppm.

11. The process of claim 1 wherein the amount of perfluoro-2-methyl-2-pentene is reduced to less than 100 ppm.

12. The process of claim 1 wherein perfluoro-2-methyl-2-pentene is converted to $(CF_3)_2C=C(O^-)CF_2CF_3$ and/or $(CF_3)_2CH-C(OR)(O^-)CF_2CF_3$.

13. The process of claim 1 further comprising the step of separating the purified perfluoro-4-methyl-2-pentene by distillation.

14. The process of claim 12 further comprising the step of removing the $(CF_3)_2C=C(O^-)CF_2CF_3$ and/or $(CF_3)_2CH-C(OH)(O^-)CF_2CF_3$ by aqueous washing.

15. A process of preparing dimers of hexafluoropropene comprising the steps of:
   a) dimerizing a solution of hexafluoropropene in the presence of a catalyst and a polar, aprotic solvent to produce a mixture of HFP dimers containing perfluoro-2-methyl-2-pentene, then
   b) treating the mixture of HFP dimers by the process of claim 1 to reduce the amount of perfluoro-2-methyl-2-pentene to less than 1000 ppm.

16. The process of claim 15 wherein said catalyst is selected from the group consisting of the cyanide, cyanate, and thiocyanate salts of alkali metal, quaternary ammonium, and quaternary phosphonium cations.

17. The process of claim 15 wherein each said catalyst is selected from the group consisting of the cyanide, cyanate, and thiocyanate salts of potassium.

18. The process of claim 15 wherein said catalyst is potassium cyanate.

19. The process of claim 15 wherein said polar, aprotic solvent is selected from the group consisting of acyclic ethers, carboxylic acid esters, alkyl nitrites, alkyl amides, alkyl sulfoxides, alkyl sulfones, oxazolidones, and mixtures thereof.

20. The process of claim 15 wherein said polar, aprotic solvent is selected from the group consisting of dimethyl sulfoxide, N,N-dimethylformamide, ethylene glycol dimethyl ether, diethylene glycol dimethyl ether, acetonitrile, and mixtures thereof.

21. The process of claim 15 wherein said polar, aprotic solvent is acetonitrile.

22. The process of claim 15 wherein said process further comprises the step of recovering the resulting hexafluoropropene dimer product, wherein the amount of perfluoro-2-methyl-2-pentene is less than 1000 ppm.

23. The process of claim 15 wherein said process further comprises the step of separating cis- and trans-perfluoro-4-methyl-2-pentene from the treated mixture.

* * * * *

UNITED STATES PATENT AND TRADEMARK OFFICE
CERTIFICATE OF CORRECTION

PATENT NO. : 7,053,253 B1
APPLICATION NO. : 11/120024
DATED : May 30, 2006
INVENTOR(S) : Zhongxing Zhang It is certified that error appears in the above-identified patent and that said Letters Patent is hereby corrected as shown below:

Title Page,
Item [56], under "Other Publications", in the "Probst et al." reference, delete "2 Methyl" and insert -- 2-Methyl --, therefor.

Column 4,
Line 51, delete "tbutyl" and insert -- t-butyl --, therefor.

Column 5,

Line 25-27, in Structure III, delete " $(CF_3)_2\tilde{C}=\overset{\overset{O}{\|}}{C}-CF_2CF_3$ " and

III insert -- $(CF_3)_2\tilde{C}-\overset{\overset{O}{\|}}{C}-CF_2CF_3$ --, therefor.

III

Column 7,
Line 18, Table 1, delete "(iPr)$_2$NEt*" and insert -- (i-Pr)$_2$NEt* --, therefor.

Line 36, delete "(iPr)$_2$NEt" and insert -- (i-Pr)$_2$NEt --, therefor.

Line 37, delete "1 8-" and insert -- 1,8- --, therefor.

Column 8,
Line 3, in Claim 9, delete "nitrites;" and insert -- nitriles; --, therefor.

Line 40, in Claim 12, delete "(CF$_3$)$_2$CH-C(OR)(O$^-$)CF$_2$CF$_3$" and insert -- (CF$_3$)$_2$CH-C(OH)(O$^-$)CF$_2$CF$_3$ --, therefor.

UNITED STATES PATENT AND TRADEMARK OFFICE
CERTIFICATE OF CORRECTION

PATENT NO. : 7,053,253 B1
APPLICATION NO. : 11/120024
DATED : May 30, 2006
INVENTOR(S) : Zhongxing Zhang It is certified that error appears in the above-identified patent and that said Letters Patent is hereby corrected as shown below:

Column 9,
Line 1, in Claim 19, delete "nitrites," and insert -- nitriles, --, therefor.

Signed and Sealed this

Second Day of December, 2008

JON W. DUDAS
*Director of the United States Patent and Trademark Office*